(12) United States Patent
Nikiforidis

(10) Patent No.: US 11,591,540 B2
(45) Date of Patent: Feb. 28, 2023

(54) METHOD FOR THE PREPARATION OF DRIED OLEOSOMES

(71) Applicant: Wageningen Universiteit, Wageningen (NL)

(72) Inventor: Konstantinos Nikiforidis, Wageningen (NL)

(73) Assignee: Time-Travelling Milkman B.V., Wageningen (NL)

( * ) Notice: Subject to any disclaimer, the term of this patent is extended or adjusted under 35 U.S.C. 154(b) by 84 days.

(21) Appl. No.: 16/771,326

(22) PCT Filed: Dec. 18, 2018

(86) PCT No.: PCT/EP2018/085617
§ 371 (c)(1),
(2) Date: Jun. 10, 2020

(87) PCT Pub. No.: WO2019/121758
PCT Pub. Date: Jun. 27, 2019

(65) Prior Publication Data
US 2020/0339909 A1 Oct. 29, 2020

(30) Foreign Application Priority Data

Dec. 22, 2017 (EP) ..................................... 17210175

(51) Int. Cl.
| | | |
|---|---|---|
| *C11B 1/10* | (2006.01) | |
| *A23L 33/115* | (2016.01) | |
| *A61K 8/14* | (2006.01) | |
| *A61K 8/92* | (2006.01) | |
| *A61K 9/107* | (2006.01) | |
| *A61K 36/31* | (2006.01) | |
| *A61K 47/44* | (2017.01) | |
| *A61Q 19/00* | (2006.01) | |
| *C11B 3/00* | (2006.01) | |
| *C11B 3/16* | (2006.01) | |

(52) U.S. Cl.
CPC ............. *C11B 1/108* (2013.01); *A23L 33/115* (2016.08); *A61K 8/14* (2013.01); *A61K 8/922* (2013.01); *A61K 9/1075* (2013.01); *A61K 36/31* (2013.01); *A61K 47/44* (2013.01); *A61Q 19/00* (2013.01); *C11B 3/008* (2013.01); *C11B 3/16* (2013.01); *A23V 2002/00* (2013.01); *A61K 2800/10* (2013.01)

(58) Field of Classification Search
CPC . C11B 1/108; C11B 3/008; C11B 3/16; A23L 33/115; A61K 8/14; A61K 8/922; A61K 9/1075; A61K 36/31; A61K 47/44; A61Q 19/00; A23V 2800/10
See application file for complete search history.

(56) References Cited

U.S. PATENT DOCUMENTS

| | | | |
|---|---|---|---|
| 2014/0045940 A1* | 2/2014 | Gray | ....................... A23L 31/00 514/560 |
| 2016/0015049 A1* | 1/2016 | Kapchie | ................... A23G 1/32 426/594 |
| 2016/0038450 A1 | 2/2016 | Gray | |

FOREIGN PATENT DOCUMENTS

WO 2009/126301 A2 10/2009

OTHER PUBLICATIONS

EPO Third Party Observation, Patent Application No. 18826304.0, dated Jul. 20, 2021, 3 pages.
Fisk, Ian D. et al., Entrapment of a volatile lipophilic aroma compound (D-limonene) in spray dried water-washed oil bodies naturally derived from sunflower seeds (*Melianthus annus*), Food Research International 54 (2013), pp. 861-866.
Kapchie, Virginie N. et al., Enzyme-Assisted Aqueous Extraction of Oleosomes from Soybeans (*Glycine max*), Journal of Agricultural and Food Chemistry, 2008, 56, pp. 1776-1771.
Maurer, S. et al., Microencapsulation of soybean oil by spray drying using oleosomes, Journal of Physics D: Applied Physics, 49 (2016) 0540001, 16 pages.
Nikiforidis, Constantinos V., et al., Composition, properties and potential food applications of natural emulsions and cream materials based on oil bodies, Royal Society of Chemistry Advances, 2014, 4, pp. 25067-25078.

* cited by examiner

*Primary Examiner* — Kyung S Chang
(74) *Attorney, Agent, or Firm* — Hoffmann & Baron, LLP

(57) ABSTRACT

A method for extracting naturally occurring oil bodies (oleosomes) from a material containing naturally occurring oil bodies (oleosomes) includes the steps of dispersing the material containing oleosomes in an aqueous composition to thereby obtain an aqueous dispersion of material containing oleosomes, extracting oleosomes from the aqueous dispersion of material containing oleosomes to thereby obtain a crude oleosome extract and isolating crude oleosomes from the extract by drying the crude oleosome extract. The dried oleosome powder may be used with a personal care product, a pharmaceutical product or a food product.

9 Claims, No Drawings

METHOD FOR THE PREPARATION OF DRIED OLEOSOMES

CROSS-REFERENCE TO RELATED APPLICATIONS

This application is the National Stage of International Application No. PCT/EP2018/085617, filed Dec. 18, 2018, which claims the benefit of European Application No. 17210175.0, filed Dec. 22, 2017, the contents of which is incorporated by reference herein.

FIELD OF THE INVENTION

The present invention relates to a method for the preparation of oleosomes (oil bodies), in particular to a method for the extraction of oil bodies from natural materials and to a method for drying extracted oil bodies. The present invention further relates to dried oleosomes that are preferably in a powdered form. The present invention relates to the use of oleosomes in pharmaceutical and food applications.

BACKGROUND OF THE INVENTION

Oil-in-water emulsions are broadly used in many industrial applications for pharma, cosmetics and foods, but they have a couple of disadvantages, like the inefficient big volume and the droplet instability over time. Therefore, if the water phase could be evaporated while the oil droplets remain stable, the benefits of their use would be greatly enhanced. However, drying of an emulsion is a rather complex and not that straightforward process. And even when a dried emulsion is obtainable, it is hard to stabilise oil droplets against oxidation or prevent the macroscopic separation of the liquid phase. To enhance the stability of the dried oil droplets typically hydrophilic carriers are necessary in order to cover and protect the oil droplets. The carriers are typically applied in amounts varying from 30 to 80 wt % of the total final powder weight. Apart from the addition of carrier, multiple process steps are commonly required, leading to expensive and not green labelled products. Typical examples of hydrophilic carriers that are commonly used at industrial scale are lactose, starch and maltodextrin.

Currently there are efforts to find sustainable and financially affordable processes to overcome the problems associated with the addition of extra carriers. A possible alternative path is to fabricate oil droplet interfaces with an appropriate elasticity that can survive the shear forces and elevated temperatures required during spray drying. Examples are the ionic complexation of polyelectrolytes on the oil droplet interface or the absorption of surfactant/biopolymer mixtures.

Another known path to fabricate oil droplets that can withstand the drying conditions is the thermal or enzymatic cross-linking of the biopolymers on the interface, although the dried droplet stability during storage is not so promising. Additionally, the main downside of the alternative proposed drying paths is the relative complexity of the processes. Therefore, upscaling is an issue and also the products may not be obtained in a grade that is suitable for pharma, food or cosmetics.

US2016/0038450 describes a process for the extraction of oleosomes, wherein the oil bodies are extracted from an aqueous dispersion. The thus obtained crude oil bodies are combined with maltodextrin as a carrier and spray dried to obtain an oleosome powder.

SUMMARY OF THE INVENTION

The present inventor has found a novel path to produce dried oleosomes by relying on drying the natural encapsulated form (oil bodies/oleosomes). The method is a simpler process route than the previously described methods that use added carriers or other means to stabilize the oleosomes.

In the broadest aspect of the invention, the initial aqueous oil body extract, containing oil bodies and extrinsic material was directly spray dried to produce stable dried oil body particles. The final powder was a natural product (no additives applied) that is stable for long term storage.

DETAILED DESCRIPTION OF THE INVENTION

Thus the present invention pertains to a method for extracting naturally occurring oil bodies (oleosomes) from a material containing naturally occurring oil bodies (oleosomes) comprising the steps of:

dispersing the material containing oleosomes in an aqueous composition to thereby obtain an aqueous dispersion of material containing oleosomes;

extracting oleosomes from the aqueous dispersion of material containing oleosomes to thereby obtain a crude oleosome extract;

isolating crude oleosomes from the extract by drying the crude oleosome extract.

By dispersing the natural material in an aqueous composition, a dispersion is obtained from the material and the contents of the material, typically comprising oleosomes and other biopolymers such as proteins and fibres (soluble and insoluble polysaccharides), as well as remaining solids such as hulls, shells and the like that are dispersed throughout the aqueous composition. The aqueous dispersion can be subjected to an extraction process in which the oleosomes are extracted from the dispersion to provide a crude oleosome extract. In the method of the invention it is preferred that at least part of the biopolymers present in the material is extracted with the oleosomes, thus forming part of the crude oleosomes extract.

Without being bound by theory, these biopolymers are capable of providing an extra protective film around the oleosomes. In plants, oils and fats are mostly present intracellularly in a form of separated entities, called oil bodies or oleosomes. Oils and fats comprise the core of these bodies, whereas they are typically surrounded by a film of proteins and may be embedded in a phospholipid monolayer.

The extraction is preferably by filtration wherein the filtration is selected from amongst passive filtration and reduced pressure filtration. Passive filtration is a filtration carried out at atmospheric pressure. In certain embodiments, pressurised filtration may be used, with pressures up to 25 bar, preferably up to 10 bar, more preferably up to 5 bar.

In one embodiment, the retentate may be redispersed in an aqueous composition and again extracted. This may lead to a higher yield in oleosomes.

In certain embodiments, the filtration may be followed by a centrifugation step at relative low speeds such as with g-forces below 8000 g. In this way, part of the fibers are removed, from the filtrate end hence enrich the filtrate in oil bodies and proteins. When the filtrate was centrifuged with g-forces exceeding 8000 g, less good results were obtained and typically no dried oleosome could be obtained.

The thus obtained crude oleosomes can now be isolated from the extract by drying the crude oleosome extract. The dried oleosomes obtained from the drying process can be in the form of a powder, preferably a naturally flowing powder that is stable for more than 6 months.

The process of the invention is advantageous since it provides dried oleosomes that can be used as such in all emulsion-based applications. The method of the invention is environmental friendly since no organic solvent aided plant oil extraction, no emulsification step and no additives are necessary. At the same time, the oil is of high quality since it keeps all its naturalness and is well protected, as the natural interfacial film of oil bodies provides higher protection than any other type of artificial oil/water interface. The present invention of directly drying the initial oil body extract without the addition of carriers provides stable oil containing particles from an initial oil body extract and provides the required stability upon long term storage. This greatly facilitates industrial application as an alternative to more "artificial" emulsions.

The oil bodies may be recovered from the material containing them into an aqueous preparation by grinding the material in a water based medium in which the pH, viscosity and ionic strength can be controlled, if necessary or desired filtering out the larger material, and then centrifuging the filtrate.

The crude oleosome extract is preferably not washed or further cleaned, but is used as it is obtained from the extraction process. In certain preferred embodiments, the drying step is performed directly on the extract. Thus, the method contains the steps of extracting oleosomes from the aqueous dispersion of material containing oleosomes to thereby obtain a crude oleosome extract and drying the thus obtained crude oleosome extract without intermediate steps between the obtainment of the crude oleosome extract and the drying of the extract to obtain the oleosomes.

In a preferred embodiment, the extract directly obtained from the aqueous dispersion is subjected to filtration and directly (spray) dried.

In a further embodiment, the extract is dried. Drying can be achieved by any conventional means, preferably selected from amongst spray drying, freeze drying, vacuum drying, but there is a preference for spray drying.

In a preferred embodiment, the drying is carried out on the crude oleosome extract directly, preferably without additives and preferably without the addition of carriers such as maltodextrin.

The aqueous composition is preferably water. The aqueous composition may contain salts, buffers and/or acid/base compounds to regulate the pH. Preferably, the aqueous composition has a pH of between 2 and 10. The aqueous composition may further contain additives to control the viscosity.

The material containing the, preferably naturally occurring, oil bodies can be selected from one or more of seeds, pollen, flowers, roots and stems of flowering plants, the spores and vegetative organs of non-flowering plants, algae, microalgae, animal cells, fungi and protists. Preferably in this invention the oil bodies are extracted from seeds or nuts, more preferably from seeds.

The seeds or nuts may be seeds, nuts or kernels from one or more of the following plants, sunflower, soybean, oil palm, safflower, almond, macadamia, cotton seed, ground nut, coconut, oil seed rape, echium, borage, linseed/flax/ hemp, evening primrose, rice, wheat, oat, maize and barley. Particularly preferred are sunflower, soybean, oil seed rape, flax and maize.

The material containing the oil bodies used in the method of the invention could all be from the same source or it could be a mixture from different sources. For example, more than one type of seed could be used, or combinations of seeds and nuts.

The dried oil bodies could all be derived from the same source material or from a mixture of sources, such as sunflower seeds and hazel nuts.

Oil bodies are organelles sometimes also referred to as oil droplets, lipid droplets, oleosomes or spherosomes.

The spray drying can be performed at any rate and can be dependent on the used equipment. In the present invention good results were obtained with an air flow rate of between 30 and 80 $m^3/h$.

The spray drying can be performed at a temperature between 60 and 200 degrees Celsius.

The dried oleosomes according to the invention are preferably in a powder form. The powder form is preferably free flowing.

The dried oleosome powders made by the method of the invention may be rehydrated for use or may be used in the dried/powder form.

The solids content of the oleosomes-based solids of the invention may vary between 85 and 100 wt %, including the oil content. Wt % are drawn on the composition of dried oleosomes.

The protein content of the oleosomes of the invention may vary between 20 and 80 wt %.

The fibre content of the oleosomes of the invention may vary between 0 and 60 wt %.

The fat or oil content of the oleosomes of the invention may vary between 20 and 80 wt %

The oleosome powder of the invention preferably has a moisture content that is below 10 wt. %, preferably below 5 wt. %.

Preferably the dried oleosomes can be stored without phase separation, oxidation and/or microbial spoilage for at least 6 months, preferably at least a year, preferably at least 18 months, preferably at least 2 years. The oil bodies may be stored at 4° C., 5° C. or at room temperature. Preferably the dried oil bodies can be stored at room temperature for at least 6 months. In a preferred embodiment, the dried oleosomes have a moisture content of less than 5 wt. % and are stable for more than 18 months when stored at room temperature.

Preferably the dried oil bodies produced by the method of the invention are able to be rehydrated to produce a stable suspension of oil bodies. Preferably the size distribution of dried oil bodies prior to resuspension is similar to the size distribution after resuspension. This stability can be determined by calculating the percentage overlap between two size distribution graphs. This overlap is preferably more than 90%, more preferably more than 95% and most preferably more than 99%.

According to a further aspect, the invention provides oleosomes, preferably in the form of a powder obtained or obtainable by the method of the invention.

According to another aspect, the invention provides a composition comprising dried oleosomes.

According to a yet further aspect, the invention provides the use of oleosomes according to the (method of the) invention in the manufacture of another product, such as a personal care product, a food product or a pharmaceutical product.

According to another aspect, the invention provides a pharmaceutical composition comprising dried oleosomes and a pharmaceutically acceptable excipient. The pharmaceutical product may be a powder, a tablet, a capsule or any other dry formulation. Alternatively, the dried oleosomes may be added dried or rehydrated to a liquid or gel or other non-dry pharmaceutical composition.

According to yet another aspect, the invention provides a food stuff or ingredient comprising dried oleosomes. Preferably the foodstuff is a dried foodstuff or ingredient, such as a cereal or a dehydrated food, or a mix of dried ingredients that include dried oleosomes that could provide their own nutritional value (for example for a baby milk formulation) and/or be loaded with primary ingredients such as natural antioxidants, vitamins, or colourants. The dried oleosomes may also be added dried or rehydrated to any other food or animal feed products.

According to another aspect, the invention provides a personal care product comprising dried oil bodies or rehydrated dried oil bodies. Personal care products may include body butters, shampoos, body lotions, body creams, sun creams etc.

According to a further aspect the invention provides the use of a dried oil body, or a rehydrated dried oil body, in the manufacture of one or more of a foodstuff, a pharmaceutical or a personal care product.

Examples

Materials and Methods
Materials

Rapeseed (*Brassica napus*) was provided by a local farmer in The Netherlands and was stored in dark vessels at 20° C. NaOH, HCl, Petroleum-ether (≥95%, ACS grade) sodium phosphate dibasic (anhydrous, ≥99.5%), sodium phosphate monobasic (≥99.0%) were purchased from Sigma-Aldrich (Germany). Methanol (99.9%, HPLC grade), chloroform (99.9%, HPLC grade) and acetone (≥99.8%) were purchased from Actu-All chemicals (the Netherlands). Diethyl ether (≥99.0%, ACS grade) and ethanol (≥95.0%, ACS grade) were purchased from Merck Millipore (Germany). Hexane (≥96%, HPLC grade) was purchased from Biosolve (France). Furthermore silica gel was provided by Supleco (USA). For the aqueous dispersions MilliQ water was used, produced by a Q-pod (Merck Millipore, Germany). Raw almonds and hazelnuts are obtained from a local store and stored in dark vessels at 20° C.

Aqueous Extraction

Rapeseed was mixed with MilliQ water in a ratio of 1/5 (w/v). The mixture was stirred with an overhead stirrer (IKA RW 20 digital with a R 1342 4-bladed propeller stirrer) for 2 h at 250 rpm, while the pH was constantly kept at 9.0 with 0.1 M NaOH. The alkaline rapeseed mixture was kept overnight at 4° C. and afterwards the mixture was blended, with a blender for 30 sec and filtered through 2 layers of cheesecloth. The retentate was re-dispersed in MilliQ water (1/5 w/v) and the pH was adjusted at 9.0. After stirring for 2 h at 250 rpm the mixture was blended once more and filtered through the 2 layers of cheesecloth. The permeates of both filtrations were combined to the final oil body emulsion, which was used as it is for spray drying.

Before drying, the emulsion was analyzed for its composition, following the official AOAC methods (AOAC, 2016). The protein conversion factor was 5.7.

Spray Drying

The oil body emulsion was spray dried through a Buchi Mini Spray Dryer (B-290), equipped with 0.7 mm nozzle. The inlet temperatures were varied between 120 and 180° C. while the air flow was kept constant at 60 m³/h. The corresponding outlet temperatures were 64, 78, 80 and 83° C. The pump was set at 10% leading to a feed flow rate of 0.15 L/h. The aspirator was set at 90% and the air flow was 40, 50 and 60 m³/h while the temperature was kept constant at 160° C.

Free Oil
Determination of Surface Free Fat

Pre-weighted powder with a known oil content was mixed with hexane at a flask (1:5). After agitation for 15 min, the sample was filtered and the oil content of the organic solvent was measured after evaporation.

Particle Size Distribution

For both the initial oil body emulsion an the re-dispersed powders, the particle size distribution was determined using dynamic light scattering (Mastersizer 2000, Malvern Instruments Ltd, UK) equipped with a wet sampler (Hydro 2000SM). The refractive index for the dispersed phase was set at 1.455.

Zeta Potential

The zeta potential of both the initial oil body emulsion an the re-dispersed powders was measured by a dynamic light scattering apparatus (DLS ZetasizerNanoZS, Malvern Instruments Ltd, UK) which was equipped with an autotitrator (MPT-2 Autotitrator, Malvern Instruments Ltd, UK) in order to measure the zeta potential as a function of pH. The pH of the emulsions were automatically adjusted using NaOH (0.1 M) and HCl (0.1 M) solutions.

Creaming Index

To observe the creaming index of the initial oil body emulsion was concentrated by centrifugation to fat content of 10 wt %, while the oil body powders were re-dispersed into water to reach the same fat content (10 wt %). The creaming index for both cases was followed for pH values between 3.0 and 9.0 over 48 hours using the following equation:

$$CI(\%) = \left(\frac{H_C}{H_T}\right) \times 100$$

$H_T$ represents the initial height of the emulsion, while $H_C$ is the lower phase volume. The heights are determined using a slide calliper (Mitutoyo No 7305, Japan).

Optical Microscopy

The morphology of the initial oil body emulsion and re-dispersed powders was analyzed using an optical microscope (Axio Scope.A1, Zeiss, Germany). The emulsion was diluted 125× before analysis, while the powders were re-dispersed in MilliQ water in a ratio of 1/2500 (w/v).

Cryo-Scanning Electron Microscope (Cryo-SEM)

The oil body powders were glued on a brass sample holder by carbon glue (Leit-C, Neubauer Chemicalien, Germany) and subsequently frozen with the use of liquid nitrogen. The sample holder was fitted into the transfer cryogenic Leica holder. All manipulations were carried out under liquid nitrogen.

The Leica sample holder was transferred in a non-dedicated cryo-preparation system (MED 020/VCT 100, Leica, Vienna, Austria) onto a sample stage at −93° C. In this cryo-preparation chamber the samples were immediately fractured and freeze-dried for 23 min at −93° C. at $1.3 \times 10^{-6}$ mBar to remove contaminating water vapour. The samples were sputter-coated with a layer of 4 nm Tungsten at the same temperature and transferred cryo-shielded into the field emission scanning microscope (Magellan 400, FEI, Eindhoven, the Netherlands) onto a sample stage equilibrated at −122° C. at $4 \times 10^{-7}$ mBar. The analysis was performed with SE at 2 kV, 13 pA.

Confocal Laser Scanning Microscope

CLSM images were obtained on a TCS SP5 device (Leica Microsystems GmbH, Germany) equipped with an inverted microscope (model Leica DMI6000), containing a set of four visible light lasers. The used objectives were HC PL APO 10×/0.40 CS and HC PL APO 20×/0.70 IMM/CORR CS. Samples were stained with Nile Blue.

The experiment is repeated with almonds and hazelnuts and provides a free flowing powder.

Comparative Experiment

The dispersion of example 1 is subjected to a filtration step through a cheesecloth. The creamy filtrate is subsequently re-dispersed in water and subjected to a centrifugation step (10400 g/20 min) at a pH of 9-9.5 and spray dried using the same equipment (Buchi Mini Spray Dryer (B-290), equipped with 0.7 mm nozzle.). the results are The droplet size was similar, but could not be spray dried and the result is an oily composition in the spray dryer tubing (free oil) that cannot be suitable spray dried and is not a powder.

The invention claimed is:

1. A method for extracting naturally occurring oil bodies being oleosomes from a material containing naturally occurring oil bodies being oleosomes comprising the steps of:

dispersing the material containing oleosomes in an aqueous composition to thereby obtain an aqueous dispersion of material containing oleosomes and biopolymers;

extracting oleosomes from the aqueous dispersion of material containing oleosomes by filtration to thereby obtain a crude oleosome extract, wherein at least part of the biopolymers present in the aqueous dispersion of material is extracted with the oleosomes to provide a crude oleosome extract surrounded by a protective film of biopolymers, wherein the oleosomes in the oleosome extract have a protein content of between 20-80 wt %; and isolating crude oleosomes from the extract by spray drying the crude oleosome extract, wherein before the isolation/drying step of the crude oleosomes from the extract no carrier chosen from lactose, starch and maltodextrin is added to stabilize the oleosomes, wherein there are no intermediate steps between obtaining the crude oleosome extract and drying the crude oleosome extract, wherein the material is selected from the group consisting of nuts, seeds and kernels, wherein the nuts, seeds and kernels are from plants selected from the group consisting of soy, sunflower, safflower, almond, macadamia, walnut, hazelnut, cotton, ground nut, peanut, coconut, rape, echium, borage, flax, evening primrose, wheat, oat, maize, and barley.

2. The method according to claim 1, wherein the extraction is by filtration, selected from the group consisting of passive filtration and reduced pressure filtration.

3. The method according to claim 1, wherein the aqueous composition is water.

4. The method according to claim 1, wherein the aqueous composition has a pH of from 2 to 10.

5. The method according to claim 1, wherein the material is from plants.

6. The method according to claim 1 wherein the spray drying is performed at a temperature between 80 and 200 degrees Celsius.

7. The method according to claim 1, wherein the spray drying is performed at an air flow rate of between 30 and 80 $m^3/h$.

8. The method according to claim 1, wherein the spray drying provides dried oleosomes in the form of a powder.

9. The method according to claim 1, wherein the nuts, seeds and kernels are from plants selected from the group consisting of soy, sunflower, safflower, flax, and maize.

* * * * *